United States Patent [19]

Moulet

[11] 3,994,282
[45] Nov. 30, 1976

[54] HEART-BEAT ELECTRONIC SIMULATOR
[75] Inventor: Camille Moulet, Le Cannet, France
[73] Assignee: Bioengineering Research, Luxembourg
[22] Filed: Apr. 10, 1975
[21] Appl. No.: 566,742

[30] Foreign Application Priority Data
Sept. 12, 1974 Italy .................................. 27208/74

[52] U.S. Cl. .................................. 128/1 C; 35/17; 46/232
[51] Int. Cl.² ........................................ A61B 19/00
[58] Field of Search ............ 35/17; 128/1 C; 46/232

[56] References Cited
UNITED STATES PATENTS
3,024,568  3/1962  Barnett .............................. 46/232
3,563,229  2/1971  Petrusson .......................... 128/1 C
3,888,233  6/1975  Ware ................................. 46/232

Primary Examiner—Louis G. Mancene
Assistant Examiner—Robert F. Cutting
Attorney, Agent, or Firm—Finnegan, Henderson, Farabow & Garrett

[57] ABSTRACT

An electronic device for simulating the human heart-beating noise comprises an astatic multivibrator, the output of which is a square wave voltage signal. This signal is given as an input to a differentiating circuit having its output connected to drive a loudspeaker diaphgram. The acoustic wave produced is similar to the human heart-beating noise.

7 Claims, 3 Drawing Figures

HEART-BEAT ELECTRONIC SIMULATOR

BACKGROUND OF THE INVENTION

The present invention relates to an electronic simulator of the heart-beat noise.

As it is well-known, new-born infants and babies of tender age have been proved to become calm and confident by listening to their mother's heart beats. However, a number of practical reasons make it impossible for a mother to constantly remain in close contact with her child.

SUMMARY OF INVENTION

It is an object of the present invention to provide an electro-acoustic device for simulating the human heart-beat noise, thus inducing in the infant the same calming and confidence-giving effects as those produced by listening to its mother's heart-beat. In particular, the present invention has the object of providing a heart-beat noise simulator, reproducing with high fidelity a phonograph recording which is authorative in the field of cardiology "The heart auscultation", by Profs. Lenegre, Coblentz and Himbert. The heart-beat noise simulator of the present invention substantially comprises an astatic multivibrator with predetermined period and cycle ratio, a differentiating circuit having as its input the output signal of said multivibrator, and a loudspeaker driven by the output signal from said differentiating circuit.

DESCRIPTION OF THE PREFERRED EMBODIMENTS

Figure 1:
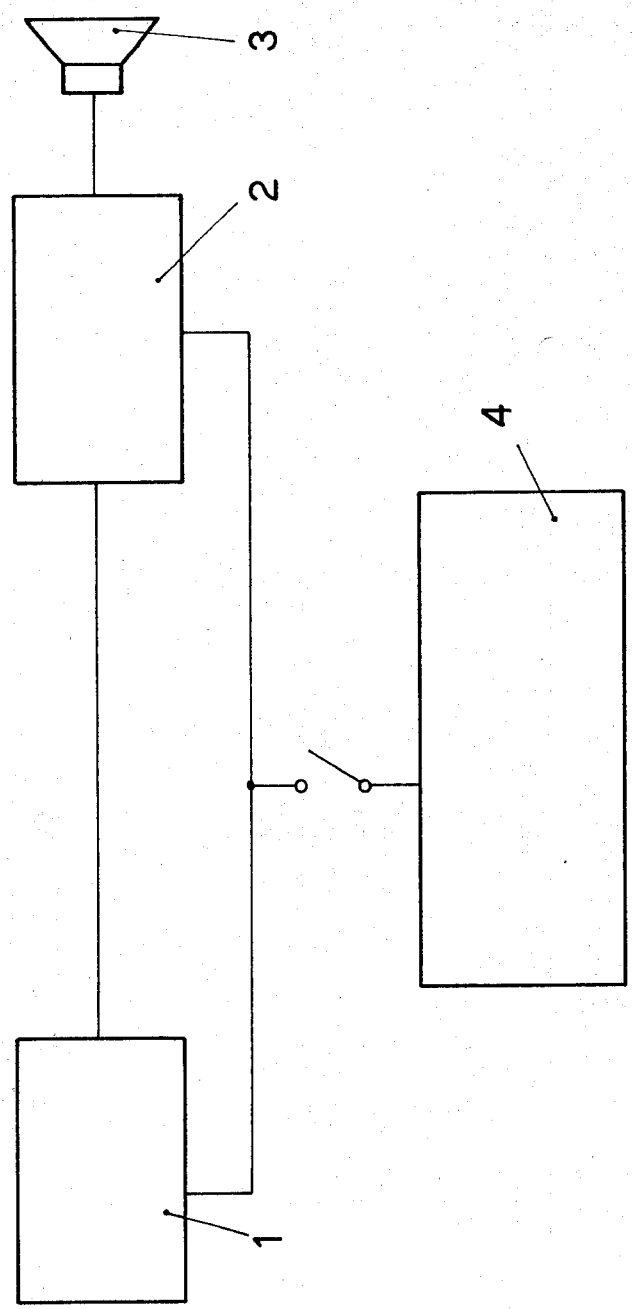
FIG. 1 is a block diagram of the circuit of a simulator according to the invention.

With reference to FIG. 1, the simulator of the invention comprises an astatic multivibrator 1, a differentiating circuit 2, a loudspeaker 3 and a power unit 4.

Multivibrator 1, as it is known, provides at its output a square wave voltage signal having constant period and cycle ratio. The differentiating unit 2 carries out the time derivative of said square wave of voltage, whereby its output shows pulses associated with quick variations of the signal given by the multivibrator. Such pulses periodically drive the loudspeaker 3 diaphragm which in connection with a proper choice of the period and cycle period of the multivibrator, produces an acoustic wave of the type represented in FIG. 3.

Power unit 4 comprises cells or batteries, preferably of Ni-Cd type, which allows the simulator to be portable during operation. Of course, the power level at the output of the astatic multivibrator 1 could be increased, if required, by insertion of an amplifier of a suitable frequency response between the multivibrator 1 and differentiating circuit 2.

Figure 2:
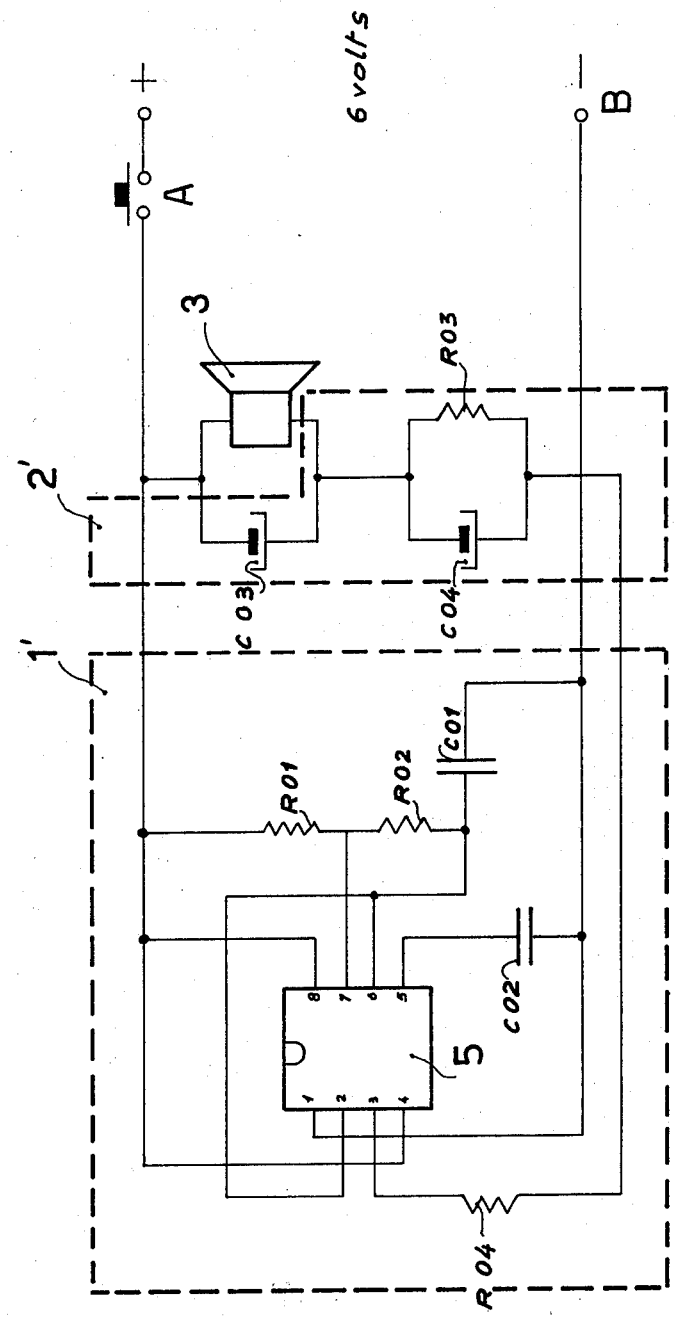
FIG. 2 shows a preferred embodiment of the circuit of FIG. 1.

Referring now to FIG. 2, in which a preferred embodiment of the diagram of FIG. 1 is illustrated (the corresponding blocks of FIG. 1 being represented by dashed lines with the same reference numerals bearing a prime notation in addition), there is shown an integrated circuit 5 connected with a R-C network comprising the resistors RO1, RO2, RO4 and the capacitors CO1, CO2. The integrated circuit 5 is available in the trade, being produced by a number of manufacturers, such as Motorola, by which it is labelled under catalogue Serial No. MC 1455.

Such integrated circuit 5, which is connected (see FIG. 2) with resistors RO1, RO2 and capacitor CO1, operates as an astatic multivibrator when terminals 2 and 6 are short-circuited.

To explain it better, the operation of the integrated circuit 5 is based on the charge of capacitor CO1 through the series of resistors RO1, RO2 and the discharge of the same through resistor RO2 which is connected between discharge point 7 and threshold point 6 of the integrated circuit.

The frequency and the oscillating cycle ratio may be precisely preset by dimensioning the two resistors RO1, RO2.

The voltage across capacitor CO1 varies between ⅔ (maximum charge) and ⅓ (maximum discharge) of the feeding voltage applied between points A, B of the circuit of FIG. 2.

The applied voltage may be comprised between 4.5V and 18 V and does not affect the oscillation frequency. The output of the integrated circuit 5 is fed through resistor RO4 to two differentiating units made of the parallel between CO4 and RO3 having connected in series the parallel between CO3 and the loudspeaker 3.

Figure 3:
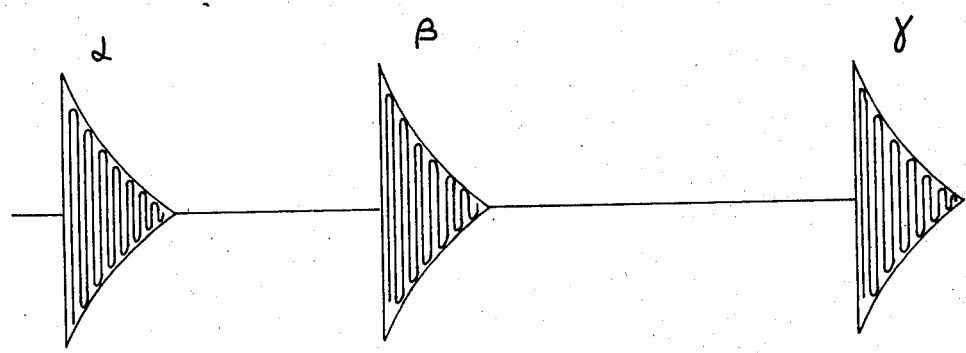
FIG. 3 shows the typical wave-form of the heart-beat noise.

If it is desired to obtain an acoustic periodic wave of the type shown in FIG. 3, wherein between the first peak and the second one there is an interval of time $t_1 = 300$ ms and between the second peak and the third peak there is an interval $t_2 = 450$ ms, it will be sufficient to give the resistors RO1, RO2 and the capacitor CO1 such values as it results:

$$300 \text{ ms} = 0.695 \text{ RO2} \times \text{CO1}$$

$$450 \text{ ms} = 0.695 \text{ (RO2 + RO1) CO1}$$

As a consequence with these values at the output of the integrated circuit 5 a square wave of period $t = 750$ ms is obtained, wherein level variations occur periodically at 300 ms and 450 ms. Such a differentiating wave gives short, periodic pulses to the diaphragm of the loudspeaker 3, which thus produces a noise quite similar to that of a human heart.

According to the described preferred embodiment, the resistance parameter of resistors RO4, RO3 is of about 20 and 2, respectively; the capacitance parameter of capacitors CO3, CO4 is of about 100 $\mu$F; and the loudspeaker 3 has an input impedance of about 8.

Finally, the loudspeaker diaphragm has a relaxation frequency of about 130 Hz.

The described circuit, provided with inner power supply, such as Ni-Cd batteries, can be arranged within a heart-shaped case and produces, as already stated, a dull sound which can be heard at a distance of some decimeters.

Therefore, the heart-beat noise simulator of the invention, placed in the cradle of an infant, produces the desired reassuring effect without disturbing the other persons of the family.

It is to be understood that, although the present invention has been described in detail with reference to the accompanying drawings representing a particularly preferred embodiment thereof additions and/or variations will be effected by those skilled in the art without exceeding the scope and the spirit of the invention itself.

What is claimed is:

1. A heart-beat simulator comprising an astatic multivibrator with predetermined period and cycle ratio for providing a square wave output signal, a differentiating circuit having as its input the square wave output signal from said multivibrator for transducing said square wave input to an output signal comprising, substantially symmetrical periodic pulses decreasing from positive and negative peaks to zero, and a loudspeaker driven by the output signal from said differentiating circuit.

2. The heart-beat simulator of claim 1 also including a power supply for direct current.

3. The heart-beat simulator of claim 1, wherein said astatic multivibrator has a period of about 750 ms with voltage transitions at about 300 ms and 450 ms.

4. The heart-beat simulator of claim 3, wherein said loudspeaker has a diaphragm with relaxation frequencies of about 130 Hz.

5. The heart-beat simulator of claim 1 wherein said differentiating circuit includes an R-C circuit and a capacitor in series and wherein said loudspeaker is connected in parallel with said capacitor.

6. A heart-beat simulator comprising an astatic multivibrator having an output with a predetermined period including two square wave pulses, the time duration between pulses of the period being longer than the time duration between the second pulse of any one period and the first pulse of the succeeding period, circuit means for differentiating the output of said multivibrator and a loudspeaker driven by the output of said differentiating circuit means, said differentiating circuit means including two R-C circuits in series, the second of said R-C circuits feeding said loudspeaker.

7. The heart-beat simulator of claim 6 wherein the second of said R-C circuits includes a capacitor in parallel with the resistance of said loudspeaker.

* * * * *